(12) United States Patent
Cantrell et al.

(10) Patent No.: US 8,436,174 B2
(45) Date of Patent: *May 7, 2013

(54) (+)-MORPHINANIUM QUATERNARY SALTS AND PROCESSES FOR THEIR PRODUCTION

(75) Inventors: Gary L. Cantrell, Troy, IL (US); Peter X. Wang, Clarkson Valley, MO (US); Bobby N. Trawick, Florissant, MO (US); Christopher W. Grote, Webster Groves, MO (US); David W. Berberich, St. Peters, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 391 days.

This patent is subject to a terminal disclaimer.

(21) Appl. No.: 12/710,379

(22) Filed: Feb. 23, 2010

(65) Prior Publication Data

US 2010/0216996 A1 Aug. 26, 2010

Related U.S. Application Data

(60) Provisional application No. 61/154,450, filed on Feb. 23, 2009.

(51) Int. Cl.
*C07D 471/22* (2006.01)
(52) U.S. Cl.
USPC ............................................................ 546/45
(58) Field of Classification Search .................. 546/45
See application file for complete search history.

(56) References Cited

U.S. PATENT DOCUMENTS

| | | | |
|---|---|---|---|
| 5,739,145 A | 4/1998 | Nagase et al. | |
| 6,174,891 B1 | 1/2001 | Nagase et al. | |
| 6,277,859 B1 | 8/2001 | Nagase et al. | |
| 2004/0077863 A1 | 4/2004 | Scammells et al. | |
| 2004/0204434 A1 | 10/2004 | Shafer et al. | |
| 2005/0182258 A1 | 8/2005 | Schmidhammer et al. | |
| 2006/0258696 A1* | 11/2006 | Moss et al. | 514/283 |
| 2007/0265293 A1 | 11/2007 | Boyd et al. | |
| 2008/0161570 A1 | 7/2008 | Perez et al. | |
| 2008/0176884 A1 | 7/2008 | Perez et al. | |
| 2008/0207669 A1 | 8/2008 | Perez et al. | |
| 2008/0214817 A1 | 9/2008 | Dlubala | |
| 2008/0234306 A1 | 9/2008 | Perez et al. | |
| 2008/0274119 A1 | 11/2008 | Moss et al. | |
| 2009/0062544 A1 | 3/2009 | Wakita et al. | |

FOREIGN PATENT DOCUMENTS

| | | |
|---|---|---|
| CH | 683 005 A5 | 12/1993 |
| DE | 1119284 | 12/1961 |
| EP | 0 418 591 | 3/1991 |
| JP | 2001-302668 | 10/2001 |
| WO | WO 01/14382 | 3/2001 |
| WO | WO 01/74819 | 4/2001 |
| WO | WO 2004/043964 | 5/2004 |
| WO | WO 2005/028483 | 3/2005 |
| WO | WO 2006/096626 | 9/2006 |
| WO | WO 2006/127899 | 11/2006 |

OTHER PUBLICATIONS

Kelentey et al., "Preparation and pharmacological properties of n-oxides of opium alkaloids", Kiserletes orvostudomany, 1958, 10(1), pp. 70-77.
Kelentey et al., "Preparation and pharmacological studies of n-oxides of opium alkaloids", Arzneimittel-Forschung, 1957, 7, pp. 594-597.
Takagi et al., "Antitussive Activity of the N-Oxides of Opium Alkaloids", Journal of the Pharmaceutical Society of Japan, 77(11), 1957 p. 1358.
Takagi et al., "Studies on Antitussives. II. Opium Alkaloids and their N-Oxides", Journal of the Pharmaceutical Society of Japan, 80(10), 1960, pp. 1501-1506.
Heumans et al., "Some aspects of the metabolism of morphine-*N*-oxide", J. Pharm. Pharmac., 1971, 23, pp. 831-836.
Bao et al., "Morphinane Alkaloids with Cell Protective Effects from *Sinomenium acutum*", J. Nat. Prod., 2005, 68, pp. 1128-1130.
Makareviche et al., "Quaternary Salts of Alkaloids", Chemistry of Natural Compounds, 2006, 42(4), pp. 473-476.
Dolle et al. (Document No. 144:397383, Caplus)2006.
Tanabe (Document No. 144:445378, Caplus)2006.

* cited by examiner

*Primary Examiner* — Samantha Shterengarts

(57) ABSTRACT

The present invention provides (+)-morphinanium quaternary salts. The invention also provides processes for producing (+)-morphinanium quaternary salts from tertiary N-substituted (+)-morphinan compounds.

8 Claims, No Drawings

(+)-MORPHINANIUM QUATERNARY SALTS AND PROCESSES FOR THEIR PRODUCTION

CROSS REFERENCE TO RELATED APPLICATIONS

This application claims priority from U.S. Provisional Application No. 61/154,450 filed on Feb. 23, 2009, which is hereby incorporated by reference in its entirety.

FIELD OF THE INVENTION

The present invention generally relates to quaternary N-substituted salts of (+)-morphinan alkaloids. In particular, the present invention provides (+)-morphinanium quaternary salts and processes for producing (+)-morphinanium quaternary salts from the corresponding tertiary N-substituted compounds.

BACKGROUND OF THE INVENTION

The (−)-morphinanium quaternary salts of opiates such as morphine and codeine have been known for over a century. Because of their ionic charge, these quaternary salts do not traverse the blood brain barrier into the central nervous system, but they do retain good to excellent affinity for peripheral opiate receptors. Consequently, the central nervous system activity of opiates responsible for pain relief is not blocked by quaternary salt derivatives of opiate antagonists, such as R-(−)-methylnaltrexone salt. Accordingly, of R-(−)-methylnaltrexone salt is used to mitigate the side effects (e.g., constipation) of systemic opiate analgesia. Recent research has shown that (−)-morphinanium alkaloid salts are potent inhibitors of vascular endothelial growth factor (VEGF). VEGF inhibitors are important adjuncts in the treatment of various tumors and the treatment of macular degeneration.

More recent work has suggested that VEGF inhibitory activity appears to be independent of the stereochemistry of the morphinan ring system. Thus, (+)-morphinanium quaternary salts may be useful as improved VEGF inhibitors because they would not interact with peripheral opiate receptors. There is a need, therefore, for processes for synthesizing quaternary salts of (+)-morphinan alkaloids.

SUMMARY OF THE INVENTION

The present invention provides (+)-morphinanium quaternary salts and synthetic processes for producing (+)-morphinanium quaternary salts from tertiary N-substituted (+)-morphinan alkaloids.

One aspect of the present invention encompasses a compound comprising Formula (II):

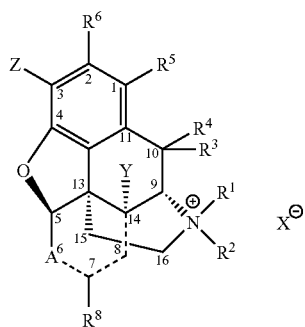

(II)

wherein:
A is selected from the group consisting of {—}C(O){-}, {—}C(=CH$_2$){—}, {—}CH$_2${—}, {—}CH(A$^1$){—}, and {—}C(A$^1$){=};
A$^1$ is selected from the group consisting of hydroxy, alkoxy, acyloxy, amido, hydrocarbyl, and substituted hydrocarbyl;
R$^1$, R$^2$, and R$^7$ are independently selected from the group consisting of hydrocarbyl and substituted hydrocarbyl;
R$^3$ and R$^4$ are independently selected from the group consisting of hydrogen, hydrocarbyl and substituted hydrocarbyl;
R$^5$ and R$^6$ are independently selected from the group consisting of hydrogen, hydrocarbyl, substituted hydrocarbyl, halogen, {—}OH, and {—}OR$^7$;
R$^8$ is selected from the group consisting of hydrogen, hydrocarbyl, and substituted hydrocarbyl;
X is an anion;
Y, if present, is selected from the group consisting of hydrogen, hydroxy, protected hydroxy, alkoxy, and acyloxy;
Z is selected from the group consisting of hydroxy, protected hydroxy, alkoxy, and acyloxy; and
the dashed lines between the carbon atoms at positions 6 and 7, 7 and 8, and 8 and 14 represent carbon to carbon bonds selected from the group consisting of (a) single bonds between all carbon atoms, wherein the carbons at positions 6 and 14 may be connected by an alkano bridge; (b) single bonds between the carbons at both positions 6 and 7 and 8 and 14, and a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

Another aspect of the invention provides a compound comprising Formula (IV):

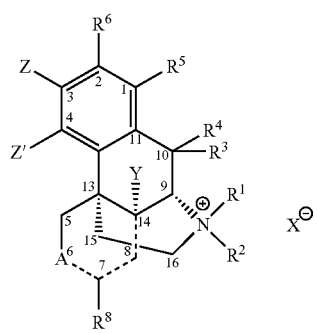

(IV)

wherein;
A is selected from the group consisting of {—}C(O){—}, {—}C(=CH$_2$){—}, {—}CH$_2${—}, {—}CH(A$^1$){—}, and {—}C(A$^1$){=};
A$^1$ is selected from the group consisting of hydroxy, alkoxy, acyloxy, amido, hydrocarbyl, and substituted hydrocarbyl;
R$^1$, R$^2$, and R$^7$ are independently selected from the group consisting of hydrocarbyl and substituted hydrocarbyl;

$R^3$ and $R^4$ are independently selected from the group consisting of hydrogen, hydrocarbyl and substituted hydrocarbyl;

$R^5$ and $R^6$ are independently selected from the group consisting of hydrogen, hydrocarbyl, substituted hydrocarbyl, halogen, {—}OH, and {—}$OR^7$;

$R^8$ is selected from the group consisting of hydrogen, hydrocarbyl, and substituted hydrocarbyl;

X is an anion;

Y, if present, is selected from the group consisting of hydrogen, hydroxy, protected hydroxy, alkoxy, and acyloxy;

Z is selected from the group consisting of hydroxy, protected hydroxy, alkoxy, and acyloxy;

Z' is selected from the group consisting of hydrogen, hydroxy, protected hydroxy, alkoxy, and acyloxy; and the dashed lines between the carbon atoms at positions 6 and 7, 7 and 8, and 8 and 14 represent carbon to carbon bonds selected from the group consisting of (a) single bonds between all carbon atoms; (b) single bonds between the carbons at both positions 6 and 7 and 8 and 14, and a double bond between the carbons at positions 7 and 8, wherein A is not {—}C(O){—} if there is a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

A further aspect of the invention provides a process for the preparation of a (+)-morphinanium quaternary salt. The process comprises contacting a (+)-morphinan comprising $NR^1$ at position 17 with $R^2X$ to form the (+)-morphinanium quaternary salt comprising $N^+(R^1)(R^2)X—$ at position 17, wherein $R^1$ and $R^2$ are independently selected from the group consisting of hydrocarbyl and substituted hydrocarbyl, and X is a leaving group.

Still another aspect of the present invention encompasses a process for the preparation of a compound comprising Formula (II). The process comprises contacting a compound comprising Formula (I) with $R^2X$ to form the compound comprising Formula (II) according to the following reaction:

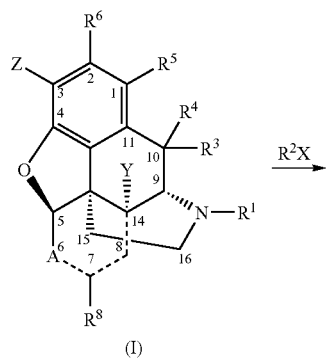

(I)

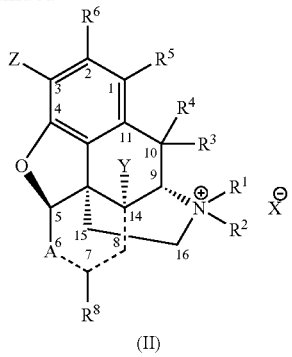

(II)

wherein:

A is selected from the group consisting of {—}C(O){—}, {—}C(=$CH_2$){—}, {—}$CH_2${—}, {—}CH($A^1$){—}, and {—}C($A^1$){=};

$A^1$ is selected from the group consisting of hydroxy, alkoxy, acyloxy, amido, hydrocarbyl, and substituted hydrocarbyl;

$R^1$, $R^2$, and $R^7$ are independently selected from the group consisting of hydrocarbyl and substituted hydrocarbyl;

$R^3$ and $R^4$ are independently selected from the group consisting of hydrogen, hydrocarbyl and substituted hydrocarbyl;

$R^5$ and $R^6$ are independently selected from the group consisting of hydrogen, hydrocarbyl, substituted hydrocarbyl, halogen, {—}OH, and {—}$OR^7$;

$R^8$ is selected from the group consisting of hydrogen, hydrocarbyl and substituted hydrocarbyl;

X is a leaving group;

Y, if present, is selected from the group consisting of hydrogen, hydroxy, protected hydroxy, alkoxy, and acyloxy;

Z is selected from the group consisting of hydroxy, protected hydroxy, alkoxy, and acyloxy; and the dashed lines between the carbon atoms at positions 6 and 7, 7 and 8, and 8 and 14 represent carbon to carbon bonds selected from the group consisting of (a) single bonds between all carbon atoms, wherein the carbons at positions 6 and 14 may be connected by an alkano bridge; (b) single bonds between the carbons at both positions 6 and 7 and positions 8 and 14, and a double bond between the carbons at positions 7 and 8; and (c) double bonds between the carbons at both positions 6 and 7 and positions 8 and 14, and a single bond between the carbons at positions 7 and 8, wherein Y is not present if there is a double bond between the carbons at positions 8 and 14.

A further aspect of the invention provides a process for the preparation of a compound comprising Formula (IV). The process comprises contacting a compound comprising Formula (III) with $R^2X$ to form the compound comprising Formula (IV) according to the following reaction:

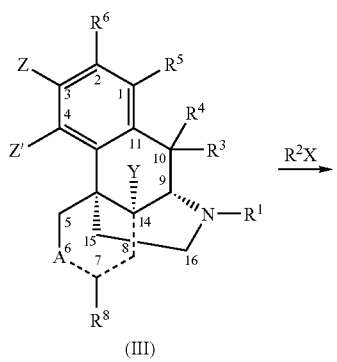

(III)

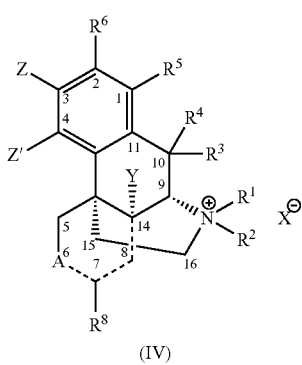

(IV)

wherein:
A is selected from the group consisting of {—}C(O){—}, {—}C(=CH₂){—}, {—}CH₂{—}, {—}CH(A¹){—}, and {—}C(A¹){=};

A¹ is selected from the group consisting of hydroxy, alkoxy, acyloxy, amido, hydrocarbyl, and substituted hydrocarbyl;

R¹, R², and R⁷ are independently selected from the group consisting of hydrocarbyl and substituted hydrocarbyl;

R³ and R⁴ are independently selected from the group consisting of hydrogen, hydrocarbyl and substituted hydrocarbyl;

R⁵ and R⁶ are independently selected from the group consisting of hydrogen, hydrocarbyl, substituted hydrocarbyl, halogen, {—}H, and {—}OR⁷;

R⁸ is selected from the group consisting of hydrogen, hydrocarbyl, and substituted hydrocarbyl;

X is a leaving group;

Y, if present, is selected from the group consisting of hydrogen, hydroxy, protected hydroxy, alkoxy, and acyloxy;

Z is selected from the group consisting of hydroxy, protected hydroxy, alkoxy, and acyloxy;

Z' is selected from the group consisting of hydrogen, hydroxy, protected hydroxy, alkoxy, and acyloxy; and the dashed lines between the carbon atoms at positions 6 and 7, 7 and 8, and 8 and 14 represent carbon to carbon bonds selected from the group consisting of (a) single bonds between all carbon atoms; (b) single bonds between the carbons at both positions 6 and 7 and 8 and 14, and a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

Other aspects and iterations of the invention are described in more detail below.

DETAILED DESCRIPTION OF THE INVENTION

The present invention provides quaternary N-substituted salts of (+)-morphinan alkaloids. Also provided are efficient processes for synthesizing quaternary N-substituted salts of (+)-morphinan alkaloids from tertiary N-substituted (+)-morphinan alkaloids. The process comprises converting the tertiary amine of a (+)-morphinan compound into a (+)-morphinanium quaternary salt.

(I) (+)-Morphinanium Quaternary Salts (a) Compounds Comprising Formula (II)

One aspect of the invention encompasses quaternary salt derivatives of (+)-morphinan compounds. In one embodiment of the invention, the compound comprises Formula (II):

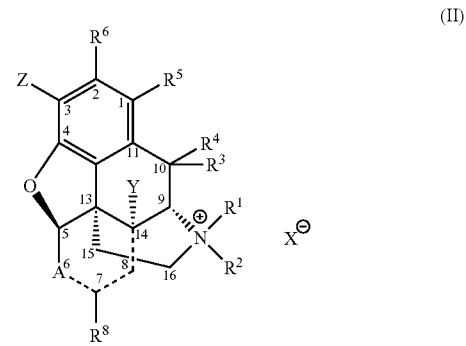

(II)

wherein:
A is selected from the group consisting of {—}C(O){—}, {—}C(=CH₂){—}, {—}CH₂{—}, {—}CH(A¹){—}, and {—}C(A¹){=};

A¹ is selected from the group consisting of hydroxy, alkoxy, acyloxy, amido, hydrocarbyl, and substituted hydrocarbyl;

R¹, R², and R⁷ are independently selected from the group consisting of hydrocarbyl and substituted hydrocarbyl;

R³ and R⁴ are independently selected from the group consisting of hydrogen, hydrocarbyl and substituted hydrocarbyl;

R⁵ and R⁶ are independently selected from the group consisting of hydrogen, hydrocarbyl, substituted hydrocarbyl, halogen, {—}OH, and {—}OR⁷;

R⁸ is selected from the group consisting of hydrogen, hydrocarbyl, and substituted hydrocarbyl;

X is an anion;

Y, if present, is selected from the group consisting of hydrogen, hydroxy, protected hydroxy, alkoxy, and acyloxy;

Z is selected from the group consisting of hydroxy, protected hydroxy, alkoxy, and acyloxy; and the dashed lines between the carbon atoms at positions 6 and 7, 7 and 8, and 8 and 14 represent carbon to carbon bonds selected from the group consisting of (a) single bonds between all carbon atoms, wherein the carbons at positions 6 and 14 may be connected by an alkano bridge; (b) single bonds between the carbons at both positions 6 and 7 and 8 and 14, and a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

As used herein, the term "substituted hydrocarbyl" refers to a hydrocarbyl moiety that is substituted with at least one heteroatom, including moieties in which a carbon chain atom is substituted with a heteroatom, provided that the heteroatom does not react with an $R^2X$ compound, as defined herein.

In preferred iterations, $R^3$, $R^4$, $R^5$, and $R^6$ are each hydrogen. $R^1$ is preferably alkyl, cycloalkyl, cycloalkylmethyl, allyl, or aryl; and even more preferably, methyl, ethyl, propyl, cyclopropylmethyl, cyclobutylmethyl, allyl, benzyl, or propargyl. $R^2$ is preferably alkyl, allyl, alkenyl, or alkaryl; and more preferably lower alkyl. In preferred iterations, X is halide, sulfate, methylsulfate, ethylsulfate, benzenesulfonate, p-toluenesulfonate, fluoroborate, fluorosulfonate, methylsulfonate, trifluoromethanesulfonate, hexachloroantimonate, hexafluorophosphate, or tetrafluoroborate. Preferred halides include bromide, chloride, fluoride, and iodide. In general, X is pharmaceutically acceptable.

In an iteration of this embodiment, the compound comprises Formula (IIa):

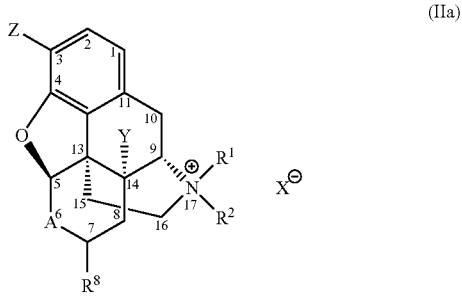

(IIa)

wherein:
A is selected from the group consisting of {—}C(O){—}, {—}C(=CH$_2$){—}, {—}CH$_2${—}, and {—}CH(A$^1$){—}, wherein the carbons at positions 6 and 14 may be connected by an alkano bridge;

$A^1$ is selected from the group consisting of hydroxy, alkoxy, acyloxy, amido, hydrocarbyl, and substituted hydrocarbyl;

$R^1$ and $R^2$ are independently selected from the group consisting of hydrocarbyl and substituted hydrocarbyl;

$R^8$ is selected from the group consisting of hydrogen, hydroxy, alkyl, substituted alkyl, alkoxy, hydrocarbyl, and substituted hydrocarbyl;

X is an anion;

Y is selected from the group consisting of hydrogen, hydroxy, alkoxy, and acyloxy; and Z is selected from the group consisting of hydroxy, alkoxy, and acyloxy.

Representative compounds comprising Formula (IIa) include quaternary salts of (+)-dihydromorphine, (+)-dihydrocodeine, (+)-hydrocodone, (+)-hydromorphone, (+)-oxycodone, (+)-oxycodeinone, (+)-oxymorphone, (+)-oxymorphinone, (+)-naloxone, (+)-naltrexone, (+)-nalbuphine, (+)-nalfurafine, (+)-nalmefene, (+)-buprenorphine, and (+)-etorphine.

In another iteration of this embodiment, the compound comprises Formula (IIb):

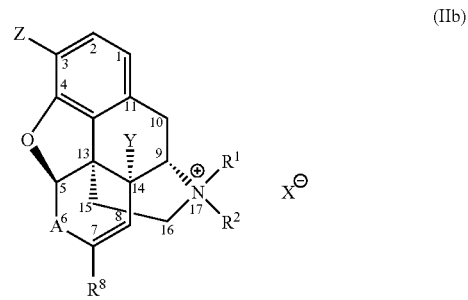

(IIb)

wherein:
A is selected from the group consisting of {—}C(O){—}, {—}C(=CH$_2$){—}, {—}CH$_2${—}, and {—}CH(A$^1$){—}; and $A^1$, $R^1$, $R^2$, $R^8$, X, Y, and Z are as defined above for compounds comprising Formula (IIa).

Representative compounds comprising Formula (IIb) include quaternary salts of (+)-morphine, (+)-codeine, and (+)-morphine-6-glucoronide.

In a further iteration, the compound comprises Formula (IIc):

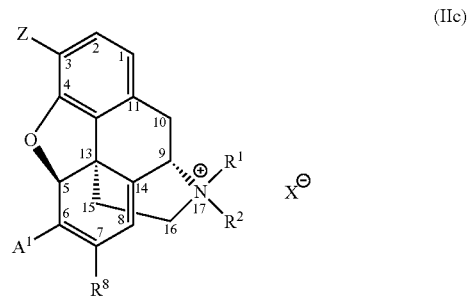

(IIc)

wherein:
$A^1$, $R^1$, $R^2$, $R^8$, X, and Z are as defined above for compounds comprising Formula (IIa).

Representative compounds comprising Formula (IIc) include quaternary salts of (+)-thebaine and (+)-oripavine.

(b) Compounds Comprising Formula (IV)

In another embodiment of the invention, the compound comprises Formula (IV):

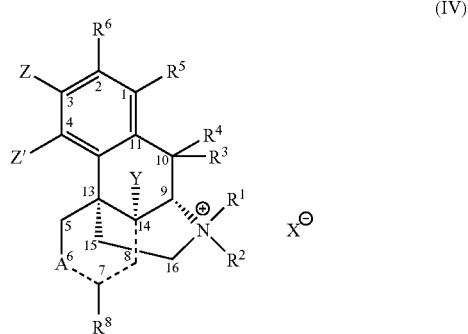

(IV)

wherein:

A is selected from the group consisting of {—}C(O){—}, {—}C(=CH$_2$){—}, {—}CH$_2${—}, {—}CH(A$^1$){—}, and {—}C(A$^1$){=};

A$^1$ is selected from the group consisting of hydroxy, alkoxy, acyloxy, amido, hydrocarbyl, and substituted hydrocarbyl;

R$^1$, R$^2$, and R$^7$ are independently selected from the group consisting of hydrocarbyl and substituted hydrocarbyl;

R$^3$ and R$^4$ are independently selected from the group consisting of hydrogen, hydrocarbyl and substituted hydrocarbyl;

R$^5$ and R$^6$ are independently selected from the group consisting of hydrogen, hydrocarbyl, substituted hydrocarbyl, halogen, {—}OH, and {—}OR$^7$;

R$^8$ is selected from the group consisting of hydrogen, hydrocarbyl, and substituted hydrocarbyl;

X is an anion;

Y, if present, is selected from the group consisting of hydrogen, hydroxy, protected hydroxy, alkoxy, and acyloxy;

Z is selected from the group consisting of hydroxy, protected hydroxy, alkoxy, and acyloxy;

Z' is selected from the group consisting of hydrogen, hydroxy, protected hydroxy, alkoxy, and acyloxy; and the dashed lines between the carbon atoms at positions 6 and 7, 7 and 8, and 8 and 14 represent carbon to carbon bonds selected from the group consisting of (a) single bonds between all carbon atoms; (b) single bonds between the carbons at both positions 6 and 7 and 8 and 14, and a double bond between the carbons at positions 7 and 8, wherein A is not {—}C(O){—} if there is a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

The term "substituted hydrocarbyl," as used herein, refers to a hydrocarbyl moiety that is substituted with at least one heteroatom, including moieties in which a carbon chain atom is substituted with a heteroatom, provided that the heteroatom does not react with an R$^2$X compound, as defined herein.

In preferred iterations, R$^3$, R$^4$, R$^5$, and R$^6$ are each hydrogen. R$^1$ is preferably alkyl, cycloalkyl, cycloalkylmethyl, allyl, or aryl; and even more preferably, methyl, ethyl, propyl, cyclopropylmethyl, cyclobutylmethyl, allyl, benzyl, or propargyl. R$^2$ is preferably alkyl, allyl, alkenyl, or alkaryl; and more preferably lower alkyl. In preferred iterations, X is halide, sulfate, methylsulfate, ethylsulfate, benzenesulfonate, p-toluenesulfonate, fluoroborate, fluorosulfonate, methylsulfonate, trifluoromethanesulfonate, hexachloroantimonate, hexafluorophosphate, or tetrafluoroborate. Preferred halides include bromide, chloride, fluoride, and iodide. In general, X is pharmaceutically acceptable.

In one iteration, the compound comprises Formula (IVa):

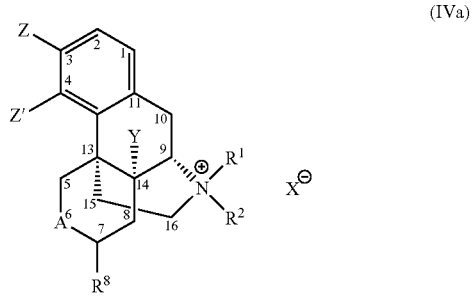

(IVa)

wherein:

A is selected from the group consisting of {—}C(O){—}, {—}C(=CH$_2$){—}, {—}CH$_2${—}, and {—}CH(A$^1$){—};

A$^1$ is selected from the group consisting of hydroxy, alkoxy, acyloxy, amido, hydrocarbyl, and substituted hydrocarbyl;

R$^1$ and R$^2$ are independently selected from the group consisting of hydrocarbyl and substituted hydrocarbyl;

R$^8$ is selected from the group consisting of hydrogen, hydroxy, alkyl, substituted alkyl, alkoxy, hydrocarbyl, and substituted hydrocarbyl;

X is an anion;

Y is selected from the group consisting of hydrogen, hydroxy, protected hydroxy, alkoxy, and acyloxy; and Z is selected from the group consisting of hydroxy, protected hydroxy, alkoxy, and acyloxy; and Z' is selected from the group consisting of hydrogen, hydroxy, protected hydroxy, alkoxy, and acyloxy.

Representative compounds comprising Formula (IVa) include quaternary salts of (+)-dextrorphan, (+)-dextromethorphan and (+)-dihydrosinomenine.

In yet another iteration, the compound comprises Formula (IVb):

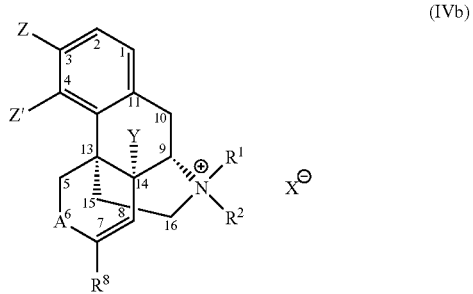

(IVb)

wherein:

A is selected from the group consisting of {—}C(=CH$_2$){—}, {—}CH$_2${—}, and {—}CH(A$^1$){—}; and A$^1$, R$^1$, R$^2$, R$^8$, X, Y, Z, and Z' are as defined above for compounds comprising Formula (IVa).

In a further iteration, the compound comprises Formula (IVc):

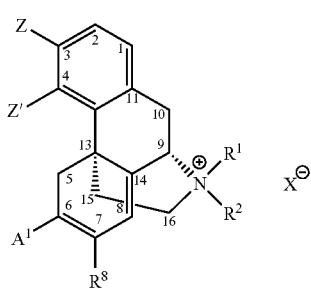

(IVc)

wherein:

A¹, R¹, R², R⁸, X, Y, Z, and Z' are as defined above for compounds comprising Formula (IVa).

The compounds comprising Formulas (II), (IIa), (IIb), (IIc), (IV), (IVa), (IVb), and (IVc) all have a (+) orientation with respect to the rotation of polarized light. More specifically, each chiral center has an R or an S configuration. In particular, the carbon at position 5, if chiral, has an S configuration, the carbon at position 13 has an R configuration, the carbon at position 14, if chiral, has an R configuration, and the carbon at position 9 has an S configuration. In each of the compounds of the invention, the nitrogen at position 17 may comprise an R or an S configuration. In some embodiments, the compound of the invention may comprise a chiral carbon at position 6, and its configuration may be R or S. In other embodiments, the compound of the invention may comprise a chiral carbon at position 7, and its configuration may be R or S.

(II) Synthesis of (+)-Morphinanium Quaternary Salts

Another aspect of the invention provides processes for the synthesis of quaternary salt derivatives of (+)-morphinan compounds. The processes comprise contacting a tertiary N-substituted (+)-morphinan compound with R²X, wherein R² is hydrocarbyl or substituted hydrocarbyl and X is a leaving group, to form the quaternary N-substituted (+)-morphinanium salt.

(a) Synthesis of Compounds Comprising Formula (II)

In one embodiment, a (+)-morphinanium quaternary salt compound comprising Formula (II) is synthesized from a (+)-morphinan compound comprising Formula (I). For purposes of illustration, Reaction Scheme 1 depicts production of a compound comprising Formula (II) in accordance with one aspect of the invention:

Reaction Scheme 1

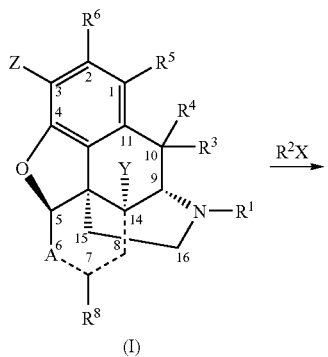

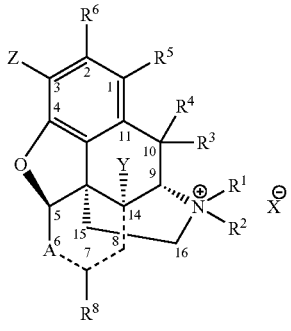

(II)

wherein:

A is selected from the group consisting of {—}C(O){—}, {—}C(=CH₂){—}, {—}CH₂{—}, {—}CH(A¹){—}, and {—}C(A¹){=};

A¹ is selected from the group consisting of hydroxy, alkoxy, acyloxy, amido, hydrocarbyl, and substituted hydrocarbyl;

R¹, R², and R⁷ are independently selected from the group consisting of hydrocarbyl and substituted hydrocarbyl;

R³ and R⁴ are independently selected from the group consisting of hydrogen, hydrocarbyl and substituted hydrocarbyl;

R⁶ and R⁶ are independently selected from the group consisting of hydrogen, hydrocarbyl, substituted hydrocarbyl, halogen, {—}OH, and {—}OR⁷;

R⁸ is selected from the group consisting of hydrogen, hydrocarbyl, and substituted hydrocarbyl;

X is a leaving group;

Y, if present, is selected from the group consisting of hydrogen, hydroxy, protected hydroxy, alkoxy, and acyloxy;

Z is selected from the group consisting of hydroxy, protected hydroxy, alkoxy, and acyloxy; and the dashed lines between the carbon atoms at positions 6 and 7, 7 and 8, and 8 and 14 represent carbon to carbon bonds selected from the group consisting of (a) single bonds between all carbon atoms, wherein the carbons at positions 6 and 14 may be connected by an alkano bridge; (b) single bonds between the carbons at both positions 6 and 7 and positions 8 and 14, and a double bond between the carbons at positions 7 and 8; and (c) double bonds between the carbons at both positions 6 and 7 and positions 8 and 14, and a single bond between the carbons at positions 7 and 8, wherein Y is not present if there is a double bond between the carbons at positions 8 and 14.

The term "substituted hydrocarbyl," as used herein, refers to a hydrocarbyl moiety that is substituted with at least one heteroatom, including moieties in which a carbon chain atom is substituted with a heteroatom, provided that the heteroatom does not react with an R²X compound, as defined herein.

In preferred iterations, R³, R⁴, R⁵, and R⁶ are each hydrogen. R¹ is preferably alkyl, cycloalkyl, cycloalkylmethyl, allyl, or aryl; and even more preferably, methyl, ethyl, propyl, cyclopropylmethyl, cyclobutylmethyl, allyl, benzyl, or proparyl. R² is preferably alkyl, allyl, alkenyl, or alkaryl; and more preferably lower alkyl. In preferred iterations, X is halide, sulfate, methylsulfate, ethylsulfate, benzenesulfonate, p-toluenesulfonate, fluoroborate, fluorosulfonate, methylsulfonate, trifluoromethanesulfonate, hexachloroantimonate, hexafluorophosphate, or tetrafluoroborate. Preferred halides include bromide, chloride, fluoride, and iodide. In general, X is pharmaceutically acceptable.

In one iteration of this embodiment, the compound comprising Formula (II) comprises Formula (IIa). For purposes of illustration, Reaction Scheme 2 depicts production of the compound comprising Formula (IIa) in accordance with this aspect of the invention:

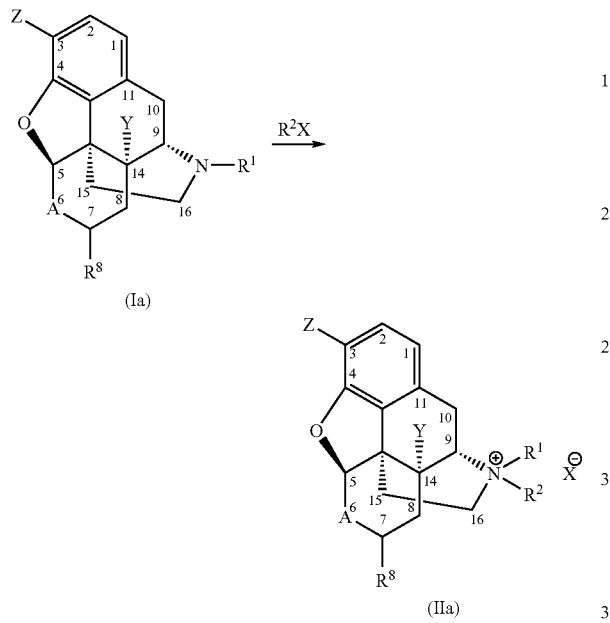

Reaction Scheme 2

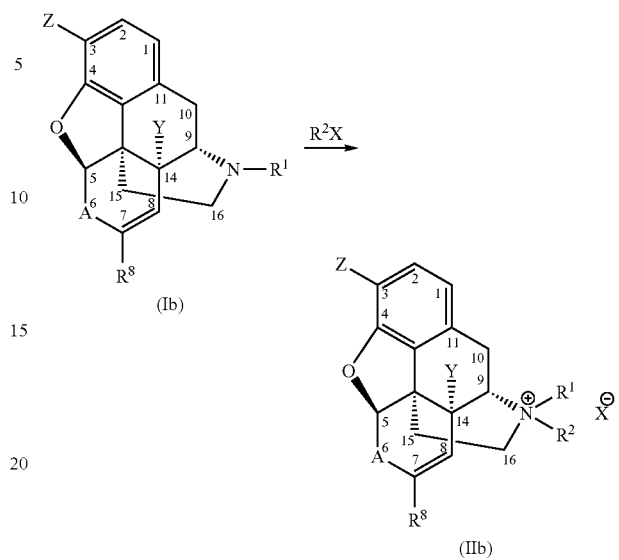

Reaction Scheme 3 wherein:
A is selected from the group consisting of {—}C(O){—}, {—}C(=CH$_2$){—}, {—}CH$_2${—}, and {—}CH(A$^1$){—}, wherein the carbons at positions 6 and 14 may be connected by an alkano bridge;
A$^1$ is selected from the group consisting of hydroxy, alkoxy, acyloxy, amido, hydrocarbyl, and substituted hydrocarbyl;
R$^1$ and R$^2$ are independently selected from the group consisting of hydrocarbyl and substituted hydrocarbyl;
R$^8$ is selected from the group consisting of hydrogen, hydroxy, alkyl, substituted alkyl, alkoxy, hydrocarbyl, and substituted hydrocarbyl;
X is a leaving group;
Y is selected from the group consisting of hydrogen, hydroxy, alkoxy, and acyloxy; and
Z is selected from the group consisting of hydroxy, alkoxy, and acyloxy Representative compounds comprising Formula (IIa) include quaternary salts of (+)-dihydromorphine, (+)-dihydrocodeine, (+)-hydrocodone, (+)-hydromorphone, (+)-oxycodone, (+)-oxycodeinone, (+)-oxymorphone, (+)-oxymophinone, (+)-naloxone, (+)-naltrexone, (+)-nalbuphine, (+)-nalfurafine, (+)-nalmefene, (+)-buprenorphine, and (+)-etorphine.

In another iteration of this embodiment, the compound comprising Formula (II) comprises Formula (IIb). Reaction Scheme 3 depicts the synthesis of the compound comprising Formula (IIb) in accordance with this aspect of the invention:

wherein:
A is selected from the group consisting of {—}C(O){—}, {—}C(=CH$_2$){—}, {—}CH$_2${—}, and {—}CH(A$^1$){—}; and
A$^1$, R$^1$, R$^2$, R$^8$, X, Y, and Z are as defined above for Reaction Scheme 2.

Representative compounds comprising Formula (IIb) include quaternary salts of (+)-morphine, (+)-codeine, and (+)-morphine-6-glucoronide.

In yet another iteration of this embodiment, the compound comprising Formula (II) comprises Formula (IIe). For illustrative purposed, Reaction Scheme 4 depicts the production of the compound comprising Formula (IIc) in accordance with this aspect of the invention:

Reaction Scheme 4

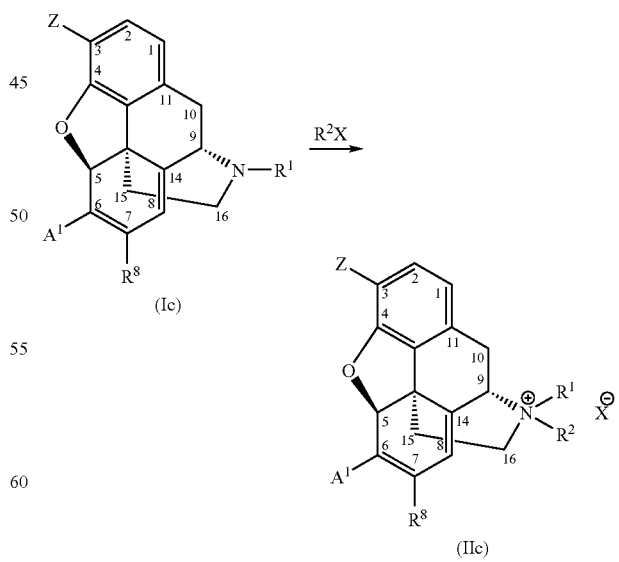

wherein:
A$^1$, R$^1$, R$^2$, R$^8$, X, and Z are as defined above for Reaction Scheme 2.

Representative compounds comprising Formula (IIc) include quaternary salts of (+)-thebaine and (+)-oripavine.

(b) Synthesis of Compounds Comprising Formula (IV)

In another embodiment of the invention, a (+)-morphinanium quaternary salt compound comprising Formula (IV) is synthesized from a (+)-morphinan compound comprising Formula (III). For purposes of illustration, Reaction Scheme 5 depicts production of a compound comprising

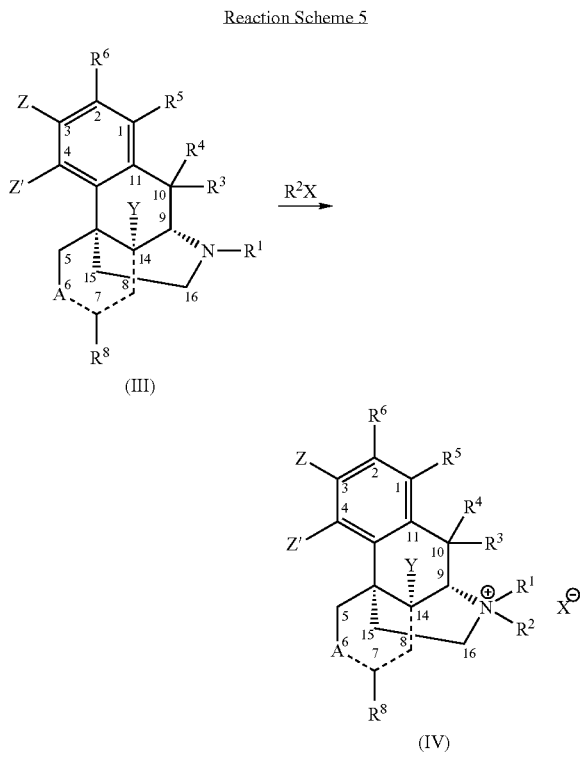

Formula (IV) in accordance with this aspect of the invention:
wherein:
A is selected from the group consisting of {—}C(O){—}, {—}C(=CH$_2$){—}, {—}CH$_2${—}, {—}CH(A$^1$){—}, and {—}C(A$^1$){=};
A$^1$ is selected from the group consisting of hydroxy, alkoxy, acyloxy, amido, hydrocarbyl, and substituted hydrocarbyl;
R$^1$, R$^2$, and R$^7$ are independently selected from the group consisting of hydrocarbyl and substituted hydrocarbyl;
R$^3$ and R$^4$ are independently selected from the group consisting of hydrogen, hydrocarbyl and substituted hydrocarbyl;
R$^5$ and R$^6$ are independently selected from the group consisting of hydrogen, hydrocarbyl, substituted hydrocarbyl, halogen, {—}OH, and {—}OR$^7$;
R$^8$ is selected from the group consisting of hydrogen, hydrocarbyl, and substituted hydrocarbyl;
X is a leaving group;
Y, if present, is selected from the group consisting of hydrogen, hydroxy, protected hydroxy, alkoxy, and acyloxy;
Z is selected from the group consisting of hydroxy, protected hydroxy, alkoxy, and acyloxy;
Z' is selected from the group consisting of hydrogen, hydroxy, protected hydroxy, alkoxy, and acyloxy; and the dashed lines between the carbon atoms at positions 6 and 7, 7 and 8, and 8 and 14 represent carbon to carbon bonds selected from the group consisting of (a) single bonds between all carbon atoms; (b) single bonds between the carbons at both positions 6 and 7 and 8 and 14, and a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

As used herein, the term "substituted hydrocarbyl" refers to a hydrocarbyl moiety that is substituted with at least one heteroatom, including moieties in which a carbon chain atom is substituted with a heteroatom, provided that the heteroatom does not react with an R$^2$X compound, as defined herein.

In preferred iterations, R$^3$, R$^4$, R$^5$, and R$^6$ are each hydrogen. R$^1$ is preferably alkyl, cycloalkyl, cycloalkylmethyl, allyl, or aryl; and even more preferably, methyl, ethyl, propyl, cyclopropylmethyl, cyclobutylmethyl, allyl, benzyl, or propargyl. R$^2$ is preferably alkyl, allyl, alkenyl, or alkaryl; and more preferably lower alkyl. In preferred iterations, X is halide, sulfate, methylsulfate, ethylsulfate, benzenesulfonate, p-toluenesulfonate, fluoroborate, fluorosulfonate, methylsulfonate, trifluoromethanesulfonate, hexachloroantimonate, hexafluorophosphate, or tetrafluoroborate. Preferred halides include bromide, chloride, fluoride, and iodide. In general, X is pharmaceutically acceptable.

In an iteration of this embodiment, the compound comprising Formula (IV) comprises Formula (IVa). Reaction Scheme 6 depicts the synthesis of the compound comprising Formula (IVa) in accordance with this aspect of the invention:

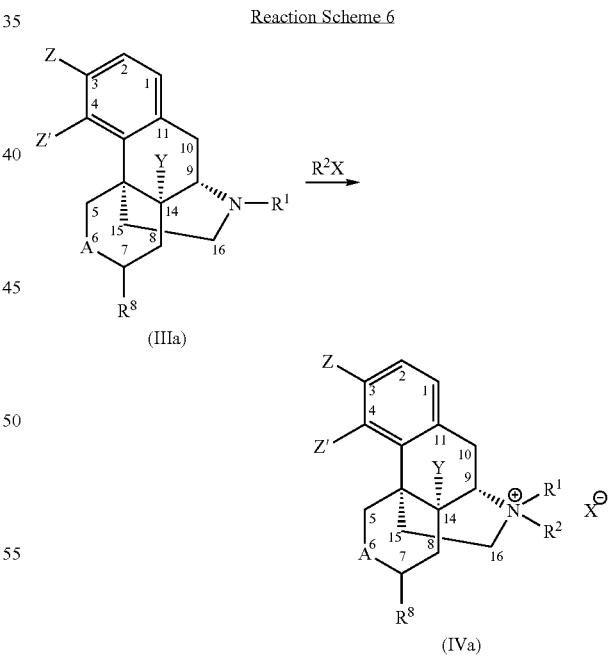

wherein:
A is selected from the group consisting of {—}C(O){—}, {—}C(=CH$_2$){—}, {—}CH$_2${—}, and {—}CH(A$^1$){—};
A$^1$ is selected from the group consisting of hydroxy, alkoxy, acyloxy, amido, hydrocarbyl, and substituted hydrocarbyl;

R¹ and R² are independently selected from the group consisting of hydrocarbyl and substituted hydrocarbyl;

R⁸ is selected from the group consisting of hydrogen, hydroxy, alkyl, substituted alkyl, alkoxy, hydrocarbyl, and substituted hydrocarbyl;

X is a leaving group;

Y is selected from the group consisting of hydrogen, hydroxy, protected hydroxy, alkoxy, and acyloxy; and Z is selected from the group consisting of hydroxy, protected hydroxy, alkoxy, and acyloxy; and Z' is selected from the group consisting of hydrogen, hydroxy, protected hydroxy, alkoxy, and acyloxy.

Representative compounds comprising Formula (IVa) include quaternary salts of (+)-dextrorphan, (+)-dextromethorphan, and (+)-dihydrosinomenine.

In another iteration of this embodiment, the compound comprising Formula (IV) comprises Formula (IVb). For purpose of illustration, Reaction Scheme 7 depicts synthesis of the compound comprising Formula (IVb) in accordance with this aspect of the invention:

Reaction Scheme 7

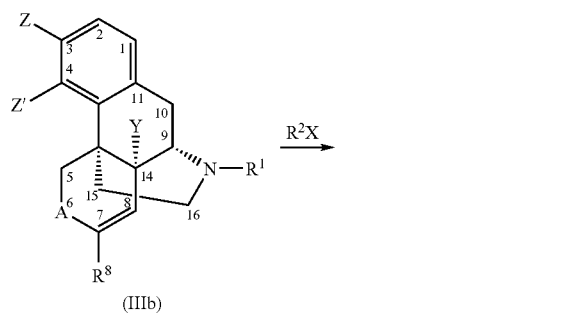

(IIIb)

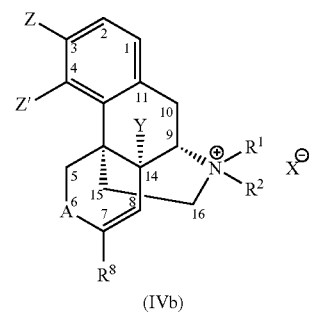

(IVb)

wherein:

A, R¹, R², R⁸, X, Y, Z, and Z' are as defined above for Reaction Scheme 6.

Representative compounds comprising Formula (IVb) include quaternary salts of (+)-sinomenine.

In a further iteration of this embodiment, the compound comprising Formula (IV) comprises Formula (IVc). Reaction Scheme 8 depicts production of the compound comprising Formula (IVc) in accordance with this aspect of the invention:

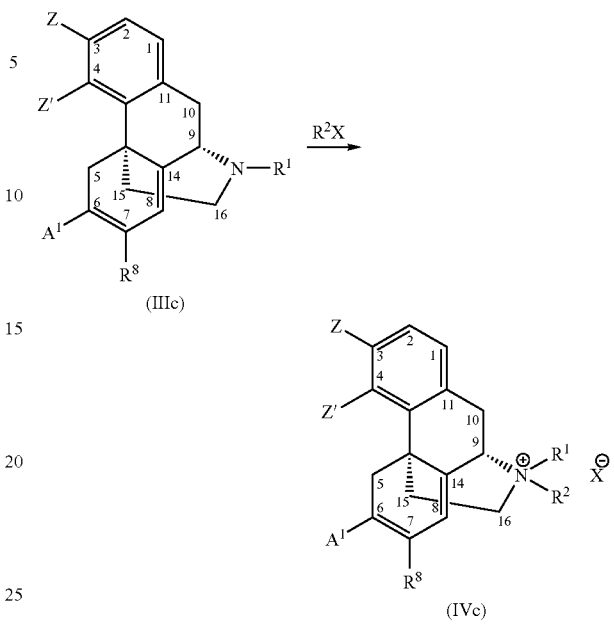

wherein:

A¹, R¹, R², R⁸, X, Z, and Z' are as defined above for Reaction Scheme 6.

(c) Reaction Mixture

The process of the invention commences with formation of a reaction mixture by combining a compound comprising Formulas (I) or (III) with R²X. Suitable R² and X groups are defined above. Thus, for example, R²X may be a methyl, ethyl, propyl, allyl, cyclopropyl, cyclopropylmethyl, propargyl, or benzyl halide or another X group as defined above. Non-limiting examples of R²X include methyl bromide, methyl chloride, allyl iodide, cyclopropylmethyl bromide, dimethyl sulfate, diethyl sulfate, di(cyclopropylmethyl) sulfate, methyl fluorosulfonate, trimethyloxonium fluoroborate, triethyloxonium fluoroborate, trimethyloxonium hexachloroantimonate, n propyl or n-octyl trifluoromethane sulfonate, trimethyloxonium hexafluorophosphate, methyl trifluoromethane sulfonate, methyl iodide, and allyl trifluoromethanesulfonate. In a preferred embodiment, R²X is methyl bromide.

The mole-to-mole ratio of the compound comprising Formulas (I) or (III) to R²X can and will vary. In general, the mole-to-mole ratio of the compound comprising Formulas (I) or (III) to R²X may range from about 1:1 to about 1:2. In some embodiments, the mole-to-mole ratio of the compound comprising Formulas (I) or (III) to R²X may be about 1:1, 1:1,1, 1:1.2, 1:1.3, 1:1.4, 1:1.5, 1:1.6, 1:1.7, 1:1.8, 1:1.9, or 1:2. In preferred embodiments the mole-to-mole ratio of the compound comprising Formulas (I) or (III) to R²X may range from about 1:1 to about 1:1.5. Furthermore, the rate of addition of R²X to the compound comprising Formulas (I) or (III) may vary. Typically, the rate of addition of R²X may range from 0.002 to about 0.02 equivalents of R²X per minute per equivalent of the compound comprising Formulas (I) or (III) in the reaction mixture.

The reaction mixture, as detailed herein, also comprises a solvent system. In general, the solvent system is anhydrous. That is, the solvent system comprises less than about 0.5% of water by weight, typically less than about 0.2% of water by weight, and in some embodiments, less than about 0.05% of water by weight. The solvent system typically comprises an aprotic solvent. Non-limiting examples of suitable aprotic solvents include acetonitrile, 1,4-dioxane, N,N-dimethylacetamide (DMAC), N,N-dimethylformamide (DMF), N-methyl-2-pyrrolidinone (NMP), hexamethylphosphoramide, (HMPA), and combinations thereof. In a preferred embodiment, the aprotic solvent is N-methyl-2-pyrrolidinone (NMP). The solvent system may additionally comprise an organic solvent such as ether, hydrocarbon, toluene, benzene, halobenzene, xylenes, or combinations thereof. In general, the solvent system comprises at least about 50% of the aprotic solvent by weight, at least about 75% of the aprotic solvent by weight, or at least about 90% of the aprotic solvent by weight.

The amount of solvent system in the reaction mixture may vary. Typically, the weight-to-weight ratio of solvent system to the compound comprising Formulas (I) or (III) may range from about 1.5:1 to about 2.0:1. In some embodiments, the weight-to-weight ratio of solvent system to the compound comprising Formulas (I) or (III) may be about 1.5:1, 1.55:1, 1.6:1, 1.65:1, 1.7:1, 1.75:1, 1.8:1, 1.85:1, 1.9:1, 1.95:1, or 2.0:1.

In some embodiments, the compound comprising Formula (I) or (III) may have an hydroxy group on position 3 (i.e., 3-hydroxy), wherein reaction with $R^2X$ may yield undesirable 3-alkyloxymorphinan compounds. To prevent such side reactions, an acid may be added to the reaction mixture to suppress ionization of the phenolic 3-hydroxy group. Suitable acids include strong mineral or organic acids. For example, the acid may be a carboxylic acid, a phosphonic acid, a sulfonic acid, or a mixture thereof. Alternatively, a small amount of a preformed alkaloid acid salt may be added to its alkaloid base in order to suppress ionization of the alkaloid base; for example, naltrexone hydrobromide may be added to naltrexone base. By way of further example, the acid may be HBr, HCl, $H_2SO_4$, $NaHSO_4$, $NaH_2PO_4$, or $Na_2HPO_4$. In preferred embodiments, the acid may be HBr gas or HCl gas. Preferably, the acid is also anhydrous. That is, the acid may comprise less that about 0.5% of water by weight, less than about 0.2% of water by weight, or more preferably, less than about 0.05% of water by weight. Those of skill in the art will also appreciate that the 3-hydroxy of the compound comprising Formulas (I) or (III) may be protected with a hydroxy protecting group prior to the reaction of the invention.

(d) Reaction Conditions

The quaternization reaction may be carried out over a wide range of temperatures and pressures. Typically, the reaction will be carried out at a temperature that ranges from about room temperature (i.e., about 25° C.) to about 90° C. In preferred embodiments, the temperature of the reaction may range from about 55° C. to about 85° C. In some embodiments, the temperature of the reaction may be about 55°, 60°, 65°, 70°, 75°, 80°, or about 85° C. In general, the reaction will be conducted at a pressure of no more than about 4 atmospheres. In preferred embodiments, the pressure of the reaction may range from about 1 to about 2 atmospheres. In other embodiment, the reaction may occur at atmospheric pressure.

The duration of the reaction can and will vary. For example, the reaction may be allowed to proceed from about several hours to about several days. Typically, however, the reaction is allowed to proceed for a sufficient period of time until the reaction is complete, as determined by means well known to those of skill in the art. In this context, a "completed reaction" generally means that the final reaction mixture contains a significantly diminished amount of the compound comprising Formulas (I) or (III) and a significantly increased amount of the compound comprising Formulas (II) or (IV) compared to the amounts of each present at the beginning of the reaction. Typically, the amount of the compound comprising Formulas (I) or (III) remaining in the final reaction mixture may be less than about 5%, and preferably less than about 1%.

When the reaction is completed, the reaction mixture is generally cooled to at least about room temperature, such that the reaction product may be isolated. In some embodiments, a solvent of lower polarity in which the reaction product is not soluble may be added to the cooled reaction mixture to facilitate precipitation of the quaternary reaction product while leaving the unreacted tertiary substrate in solution. Examples of suitable solvents include, but are not limited to acetone, chloroform, dichloromethane, ethyl acetate, propyl acetate, methyl ethyl ketone, methyl butyl ketone, ether, t-butylmethylether, 2-methyltetrahydrofuran, hydrocarbon, toluene, benzene, chlorobenzene, bromobenzene, and mixtures thereof. The reaction mixture may be optionally cooled further to about 0° C. to about 5° C. The precipitated product generally is separated from the remaining reaction mixture by filtration, and is washed and dried to produce the final product, namely the compound comprising Formulas (II) or (IV). The yield of the compound comprising Formulas (II) or (IV) typically will range form about 50% to about 99%. In some embodiments, the yield of the compound comprising Formulas (II) or (IV) may be at least about 50, 55, 60, 65, 70, 75, 80, 85, 90, or 95%.

In embodiments in which X is a halide, the compound comprising Formulas (II) or (IV) comprises a halide anion. This anion may be exchanged by treating the compound with a protic acid, thereby replacing the halide ion with another anion such as nitrate, sulfate, phosphate, or another halide ion.

Definitions

The compounds described herein may have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted home- or heterocyclic aromatic groups. These aromatic groups are preferably monocyclic, bicyclic, or tricyclic groups containing from 6 to 14 atoms in the ring portion. The term "aromatic" encompasses "aryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl is the preferred aryl.

The terms "halogen" or "halo" as used herein alone or as part of another group refer to chlorine, bromine, fluorine, and iodine.

The term "halide" refers to bromide, chloride, fluoride, or iodide ions.

The term "heteroatom" refers to atoms other than carbon and hydrogen. Examples of heteroatoms include nitrogen, oxygen, silicon, phosphorous, boron, sulfur, and halogen, provided that the heteroatom does not react with an $R^2X$ compound, as defined herein.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring, provided that the heteroatom does not react with an $R^2X$ compound, as defined herein. The heterocyclo group preferably has 1 or 2 oxygen atoms and/or 1 to 4 nitrogen atoms in the ring, and is bonded to the remainder of the molecule through a carbon or heteroatom.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting an oxygen atom, wherein the protecting group may be removed, subsequent to the reaction for which protection is employed, without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties that are substituted with at least one heteroatom, including moieties in which a carbon chain atom is substituted with a heteroatom, provided that the heteroatom does not react with an $R^2X$ compound, as defined herein.

Suitable substituents include halogen, heterocyclo, alkoxy, alkenoxy, aryloxy, hydroxy, protected hydroxy, acyl, acyloxy, nitro, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples illustrate various embodiments of the invention.

Example 1

Synthesis of R-3-Acetoxy-(+)-Naltrexone Methobromide

The following reaction scheme depicts the synthesis of 3-acetoxy-(+)-naltrexone methobromide:

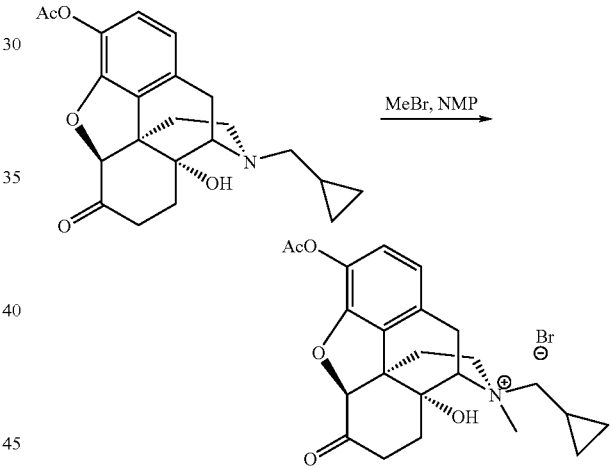

A solution of 3-acetoxy-(+)-naltrexone in 1-methyl-3-pyrrolidinone (NMP) (732.2 g of 30% wt/wt solution, 0.57 moles) may be added to a 1-L, 5-neck, jacketed pressure reactor equipped with a polished glass stirring shaft, mechanical stirrer, reflux condenser, pressure manifold, thermowell, and ⅛" (id) addition line. Methyl bromide (MeBr, 107.9 g, 1.14 moles) then may be added subsurface through the addition line with vigorous stirring of the solution over a 1-hour period. The amount of MeBr is determined by a difference in the initial and final weights of a MeBr lecture bottle. During the addition, the temperature of the reaction mixture may increase to about 33° C. (yellow solution) with a maximum pressure of 3-4 psi. After the appropriate amount of MeBr is added, the reactor headspace may be evacuated and re-pressurized with MeBr (to about 2 psi) twice before heating to 60° C. At 60° C., a pressure of 2-4 psi may be observed. The reaction mixture may be stirred overnight (15 hours) with no pressure remaining over the yellow solution. Aqueous hydrogen bromide (HBr, 1.0 equiv, 0.57 moles, 96.58 g of 48 wt. %) may be added slowly at 60° C. over a 30-minute period. The reactor may be vented into NMP in order to trap gaseous methyl bromide that is generated during the HBr addition. During the addition, the reaction temperature may increase to about 64° C. The reaction temperature then may be increased to 80° C. over a 1.5-hour period, wherein evolution of methyl bromide ceases. The mixture may be stirred at 80° C. for 2 hours, wherein precipitation occurs. After 5 hours at 80° C., the slurry may be analyzed by HPLC. Preferably, only a minor amount of 3-acetoxy-(+)-naltrexone methobromide remains in the slurry (<0.5% by area). The mixture then may be transferred to a 2-L three-neck round-bottomed flask equipped with a glass stirring shaft, mechanical stirrer, reflux condenser, and thermocouple under a nitrogen atmosphere. The mixture may be cooled to about 56° C. and methanol (512.5 g, 1.0 wt equiv. based on the amount of NMP charged) may be added quickly to facilitate crystallization of methobromide salts. The slurry then may be cooled to about 20° C. over a 30-minute period and then to about 5-10° C. in an ice bath. The slurry may be stirred for 1 hour at 5-10° C., filtered, and the product washed with cold methanol (319 mL, 1.45 mL/g of starting material to afford product as a white solid (e.g., about 236.1 g of product; 87.2%). The crude product may be analyzed by HPLC (e.g., it may contain 88.54% R and 1.47% S diastereomers).

Example 2

Synthesis of R-(+)-Naltrexone Methobromide

The following reaction scheme depicts the synthesis of (+)-naltrexone

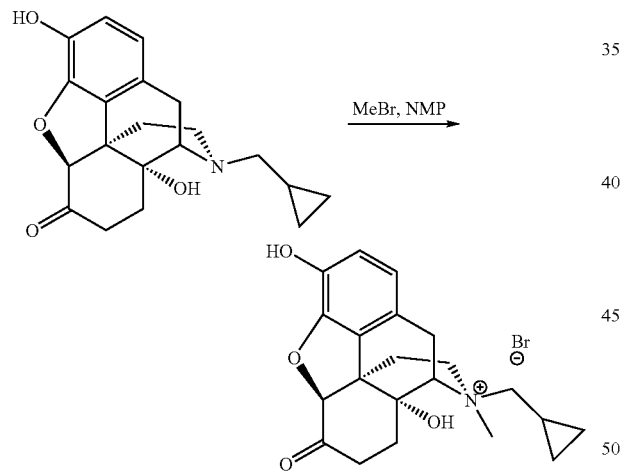

methobromide:

Fresh anhydrous 1-methyl-2-pyrrolidinone (50 mL) may be added to a 3-necked 250 mL flask fitted with a thermocouple, addition funnel, condenser, and a mechanical stirrer under a sweep of dry nitrogen. The solution may be heated to 55° C. The addition funnel may be replaced with a powder funnel and anhydrous (+)naltrexone base (39.5 grams) added with stirring. After the funnel is "washed down" with 10 mL of additional 1-methyl-2-pyrrolidinone, the temperature may be is adjusted to 55-58 ° C. and the addition funnel replaced on the flask. Separately, 10 mL of anhydrous 1-methyl-2-pyrrolidinone may be cooled in a graduated cylinder, and methyl bromide gas may be condensed in a lecture bottle using an ice bath and 10 mL measured out as a liquid into another cold graduated cylinder. The cold methyl bromide liquid and 1-methyl-2-pyrrolidinone may be combined and mixed. The methyl bromide solution may be poured into the addition funnel and added dropwise to the (+) naltrexone solution under a slow sweep of dry nitrogen. The temperature of the solution may increase to about 66° C. The reaction temperature and time may be set at 62.5° C. for nine hours. After an hour, a fine white suspension of R-(+)-naltrexone methobromide may begin to form. At the end of nine hours the heating may be discontinued and the mixture may be allowed to cool to room temperature with stirring overnight. Acetone (75 mL) may be poured into the suspension to facilitate the precipitation of product. The slurry may be cooled to ice bath temperature and stirred. The product may be recovered by vacuum filtration and washed with 25 mL of additional acetone. The product may be dried to a constant weight in a vacuum oven set at 60° C. The yield of the unpurified salts may be about 31.8 g.

Example 3

Synthesis of R-(+)-Naloxone Methobromide

Anhydrous 1-methyl-2-pyrrolidinone (5 mL) may be added to a 25 mL flask fitted with a condenser and stirring bar under a sweep of dry nitrogen. Anhydrous (+)naloxone base (4.11 grams) may be added with stirring. Methyl bromide gas may be condensed in a lecture bottle using an ice bath and 0.5 mL measured out as a liquid in another cold graduated cylinder. The methyl bromide may be poured into the naltrexone base suspension under a slow sweep of dry nitrogen. The reaction temperature and time may be set at 60° C. for ten hours. At the end of ten hours the heating may be discontinued and the mixture allowed to cool to room temperature with stirring overnight (or longer). Acetone (10 mL) may be added to the suspension to facilitate the precipitation of the product. The slurry may be cooled to ice bath temperature with stirring. The product may be recovered by vacuum filtration and washed with additional acetone. The product may be dried in a vacuum oven set at 60° C. for two hours. For example, 2.89 grams of the crude product may be recovered. Recrystallization from methanol/water (20 30 mL, 8:2) may yield 2.43 grams of a white crystalline salt.

Example 4

Synthesis of R(+)-Nalfurafine Methoiodide (+)-Nalfurafine (2.0 g, 4.3 mmol), ethyl acetate (60 mL), methanol (6 mL), and methyl iodide (1.3 mL) may be placed together in a sealed reactor. The reactor contents may be stirred at 100° C. for about four days. Methanol (60 mL) may be added to the reaction solution to facilitate precipitation of the product. The precipitated solid may be dissolved and concentrated. Distilled water (400 mL) may be added to the resulting residue. This aqueous solution may be washed with chloroform (7×100 mL). The water phase may be concentrated. The resulting residue may be recrystallized from ethyl acetate-methanol. The resulting crystal may be dissolved in distilled water (500 mL). This aqueous solution may be washed with chloroform (3×100 mL). The water phase may be concentrated. The resulting residue may be recrystallized three times from methanol. As an example, 102 mg of the product, R-(+)-nalfurafine methoiodide, may be obtained.

Example 5

Synthesis of R-(+)-Oxycodone Cyclopropylmethobromide

The following reaction scheme depicts the synthesis of (+)-oxycodone cyclopropylmethobromide:

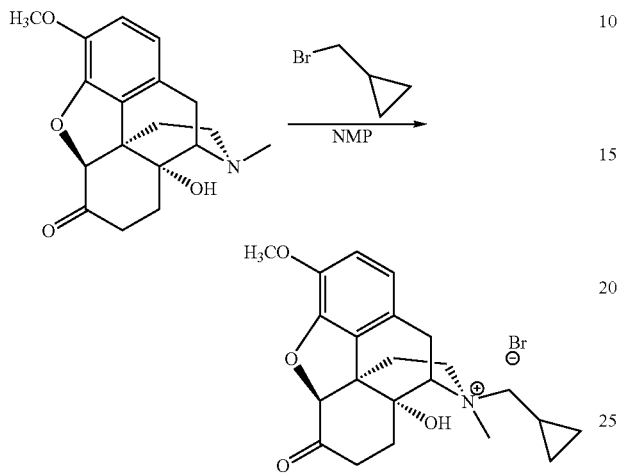

A reactor was charged with (+)-oxycodone (0.5 g, 1.595 mmol) and 2 mL of 1-methyl-3-pyrrollidinone (NMP). The reactor was flushed with nitrogen and the mixture was kept under nitrogen throughout the reaction. Cyclopropylmethylbromide (0.2 mL, 1.3 eq) was added and the reaction mixture was heated to 68° C. for 3 h. Samples were removed at 1 h, 2 h, and 3 h for analysis; the reaction was complete after 2 h. The reaction mixture was cooled to room temperature. Acetone (4 mL) was added and the mixture was stirred at 20° C. for 1 h. The solids were filtered and washed with acetone (3×2 mL); 0.2 g of solid was recovered. The filtrate and acetone wash were pumped down (and washed with water) to give another 0.22 g of solid. The solids were combined, charged with water (5 mL, stirred at rt for 2 h), and filtered. The solid was washed with water (3×2 mL), dried in a vacuum oven at 65° C. for 18 h to give 0.36 g of white solid.

What is claimed is:

1. A compound of Formula (II):

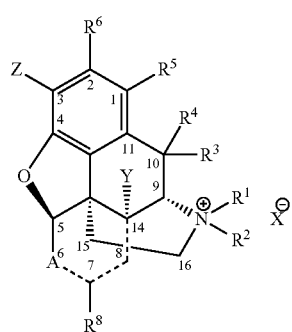

(II)

wherein:
A is chosen from {—}C(O){—}, {—}C(=CH$_2$){—}, {—}CH$_2${—}, {—}CH(A$^1$){—}, and {—}C(A$^1$){=};

A$^1$ is chosen from hydroxy, alkoxy, acyloxy, amido, hydrocarbyl, and substituted hydrocarbyl;

R$^1$, R$^2$, and R$^7$ are independently chosen from hydrocarbyl and substituted hydrocarbyl;

R$^3$ and R$^4$ are independently chosen from hydrogen, hydrocarbyl and substituted hydrocarbyl;

R$^5$ and R$^6$ are independently chosen from hydrogen, hydrocarbyl, substituted hydrocarbyl, halogen, {—}OH, and {—}OR$^7$;

R$^8$ is chosen from hydrogen, hydrocarbyl, and substituted hydrocarbyl;

X is an anion;

Y, if present, is chosen from hydrogen, hydroxy, protected hydroxy, alkoxy, and acyloxy;

Z is chosen from hydroxy, protected hydroxy, alkoxy, and acyloxy; and the dashed lines between the carbon atoms at positions 6 and 7, 7 and 8, and 8 and 14 represent carbon to carbon bonds chosen from (a) single bonds between all carbon atoms, wherein the carbons at positions 6 and 14 may be connected by an alkano bridge; (b) single bonds between the carbons at both positions 6 and 7 and 8 and 14, and a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

2. The compound of claim 1, wherein R$^1$ is chosen from alkyl, cycloalkyl, cycloalkylmethyl, allyl, and aryl; and R$^2$ is chosen from alkyl, allyl, alkenyl, and alkaryl and X is chosen from halide, sulfate, methylsulfate, ethylsulfate, benzenesulfonate, p-toluenesulfonate, fluoroborate, fluorosulfonate, methylsulfonate, trifluoromethanesulfonate, hexachloroantimonate, hexafluorophosphate, and tetrafluoroborate.

3. The compound of claim 1, wherein the compound has Formula (IIa):

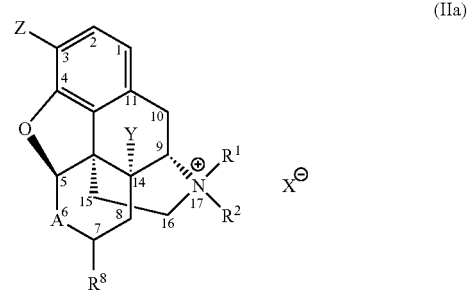

(IIa)

wherein:
A is chosen from {—}C(O){—}, {—}C(=CH$_2$){—}, {—}CH$_2${—}, and {—}CH(A$^1$){—}, wherein the carbons at positions 6 and 14 may be connected by an alkano bridge;

A$^1$ is chosen from hydroxy, alkoxy, acyloxy, amido, hydrocarbyl, and substituted hydrocarbyl;

R$^1$ and R$^2$ are independently chosen from hydrocarbyl and substituted hydrocarbyl;

R$^8$ is chosen from hydrogen, hydroxy, alkyl, substituted alkyl, alkoxy, hydrocarbyl, and substituted hydrocarbyl;

X is an anion;

Y is chosen from hydrogen, hydroxy, alkoxy, and acyloxy; and

Z is chosen from hydroxy, alkoxy, and acyloxy.

4. The compound of claim 3, wherein the compound is a quaternary salt of a compound chosen from (+)-dihydromorphine, (+)-dihydrocodeine, (+)-hydrocodone, (+)-hydromorphone, (+)-oxycodone, (+)-oxycodeinone, (+)-oxymorphone, (+)-oxymorphinone, (+)-naloxone, (+)-naltrexone, (+)-nalbuphine, (+)-nalfurafine, (+)-nalmefene, (+)-buprenorphine, and (+)-etorphine.

5. The compound of claim 1, wherein the compound has Formula (IIb):

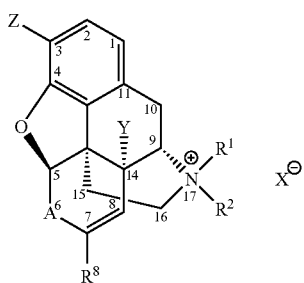

(IIb)

wherein:
- A is chosen from {—}C(O){—}, {—}C(=CH$_2$){—}, {—}CH$_2${—}, and {—}CH(A$^1$){—};
- A$^1$ is chosen from hydroxy, alkoxy, acyloxy, amido, hydrocarbyl, and substituted hydrocarbyl;
- R$^1$ and R$^2$ are independently chosen from hydrocarbyl and substituted hydrocarbyl;
- R$^8$ is chosen from hydrogen, hydroxy, alkyl, substituted alkyl, alkoxy, hydrocarbyl, and substituted hydrocarbyl;
- X is an anion;
- Y is chosen from hydrogen, hydroxy, alkoxy, and acyloxy; and
- Z is chosen from hydroxy, alkoxy, and acyloxy.

6. The compound of claim 5, wherein the compound is a quaternary salt of a compound chosen from (+)-morphine, (+)-codeine, and (+)-morphine-6-glucoronide.

7. The compound of claim 1, wherein the compound has Formula (IIc):

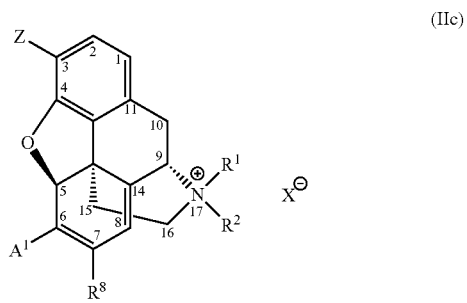

(IIc)

wherein:
- A$^1$ is chosen from hydrogen, hydroxy, alkoxy, acyloxy, amido, hydrocarbyl, and substituted hydrocarbyl;
- R$^1$ and R$^2$ are independently chosen from hydrocarbyl and substituted hydrocarbyl;
- R$^8$ is chosen from hydrogen, hydroxy, alkyl, substituted alkyl, alkoxy, hydrocarbyl, and substituted hydrocarbyl;
- X is an anion; and
- Z is chosen from hydroxy, alkoxy, and acyloxy.

8. The compound of claim 7, wherein the compound is a quaternary salt of a compound chosen from (+)-thebaine and (+)-oripavine.

* * * * *